(12) United States Patent
Atteraas et al.

(10) Patent No.: US 8,435,308 B2
(45) Date of Patent: May 7, 2013

(54) PROSTHETIC CONNECTOR

(75) Inventors: Kjetil Atteraas, Fana (NO); Gunnar Moen, Fana (NO)

(73) Assignee: Atteras Invent AS, Bergen (NO)

( * ) Notice: Subject to any disclaimer, the term of this patent is extended or adjusted under 35 U.S.C. 154(b) by 0 days.

(21) Appl. No.: 13/634,885

(22) PCT Filed: Mar. 25, 2011

(86) PCT No.: PCT/EP2011/054627
§ 371 (c)(1),
(2), (4) Date: Sep. 14, 2012

(87) PCT Pub. No.: WO2011/117390
PCT Pub. Date: Sep. 29, 2011

(65) Prior Publication Data
US 2013/0006387 A1 Jan. 3, 2013

Related U.S. Application Data

(60) Provisional application No. 61/317,312, filed on Mar. 25, 2010.

(51) Int. Cl.
*A61F 2/60* (2006.01)
(52) U.S. Cl.
USPC .............................. 623/32; 623/38
(58) Field of Classification Search ............... 623/27–38
See application file for complete search history.

(56) References Cited

U.S. PATENT DOCUMENTS

| | | | |
|---|---|---|---|
| 6,361,569 B1 * | 3/2002 | Slemker et al. | 623/33 |
| 6,511,513 B1 | 1/2003 | Laghi | |
| 6,679,921 B2 * | 1/2004 | Grubbs | 623/33 |
| 6,893,468 B2 * | 5/2005 | Lund | 623/36 |
| 7,108,722 B2 * | 9/2006 | Wagman | 623/38 |
| 2005/0216096 A1 | 9/2005 | Wagman | |
| 2005/0244220 A1 | 11/2005 | Ingimarsson | |

FOREIGN PATENT DOCUMENTS

| | | |
|---|---|---|
| DE | 202004008159 | 9/2004 |
| DE | 102005034388 | 12/2006 |
| WO | 03/041619 | 5/2003 |

OTHER PUBLICATIONS

ISR of Jun. 1, 2011 (submitted in part as statement of relevance for non-english refs).

* cited by examiner

*Primary Examiner* — Bruce E Snow
(74) *Attorney, Agent, or Firm* — Christian D. Abel

(57) ABSTRACT

A locking device for a prosthesis comprising a locking mechanism that may be disengaged from the locking pin using a single hand, and that remains in the open position until the pin is removed. The locking mechanism of the present invention thus provides a secure connection that may be more easily removed than current devices. The current invention comprises a self-holding release mechanism that makes it possible to use both hands for pulling the amputation stump out of the prosthetic sleeve. The release mechanism is held in an open position by an interior locking mechanism. When the locking pin has come out of the locking mechanism, the inner locking mechanism will let the release device return and the lock will reset, and again be ready for use when the locking pin is inserted once more.

8 Claims, 7 Drawing Sheets

PROSTHETIC CONNECTOR

FIELD OF THE INVENTION

The invention relates to prosthetics, more specifically to a prosthetic lock having a self-holding release mechanism with automatic resetting based on a locking pin. The lock is used to connect a prosthetic limb to an amputation stump about which is worn a silicon stocking having a locking pin.

BACKGROUND

Amputees use prosthetic limbs. In the case of for example a leg prosthesis, a silicon flexible stocking is pulled over the amputation stump. This stocking is equipped with a locking pin at its lower end. This pin engages a locking mechanism in the prosthesis to hold it securely in place.

With known devices, at the present time it is only possible to release the locking pin by pressing and holding a release button on the locking mechanism until the locking pin is clear of the locking mechanism. The result is that only one hand is free to be used on the actual prosthetic sleeve when it has to be pulled off. This is a problem for users who are in poor health, have injured hands or only one hand and where the silicon liner is a tight fit in the prosthetic sleeve.

SUMMARY OF THE INVENTION

The present invention provides a locking device for a prosthesis comprising a locking mechanism that may be disengaged from the locking pin using a single hand, and that remains in the open position until the pin is removed. The locking mechanism of the present invention thus provides a secure connection that may be more easily removed than current devices. The current invention comprises a self-holding release mechanism that makes it possible to use both hands for pulling the amputation stump out of the prosthetic sleeve. The release mechanism is held in an open position by an interior locking mechanism. When the locking pin has come out of the locking mechanism, the inner locking mechanism will let the release device return and the lock will reset, and again be ready for use when the locking pin is inserted once more.

The locking mechanism of the present invention allows the user to disengage the locking pin from the lock by means of a release button that holds the locking mechanism in a disengaged state until the pin is removed. This is achieved according to the invention by a release button connected to a movable release device having a steel pin. The steel pin is arranged to push up a locking arm which is spring-loaded. When the release button is pressed inward, the pin pushes past the locking arm, which then snaps back into its original position, engages the pin and holds the release button in an inner position. The release button is also in connection with a locking dowel. The locking dowel engages teeth in locking pin when the prosthesis is in use. Because they are connected, when the release button is held in the inner position, the locking dowel is held in a disengaged position, out of engagement with locking pin.

The locking arm is also connected to a sensor pin which has contact with the locking pin when the latter is in the lock and in a locked position. This sensor pin keeps the locking arm in a position that blocks the return of the release button while the locking pin is in the lock. When the locking pin is removed from the lock, it becomes possible for the sensor pin (15) to enter the hole vacated by the locking pin. This in turn will move the locking arm (13) to a position which will free the steel pin and allow the release button to return to its outer position. This allows the locking dowel to move into a position where the lock will be "active" and ready to engage locking pin the next time the user inserts it into the locking device.

DETAILED DESCRIPTION OF THE INVENTION

Figure 6:
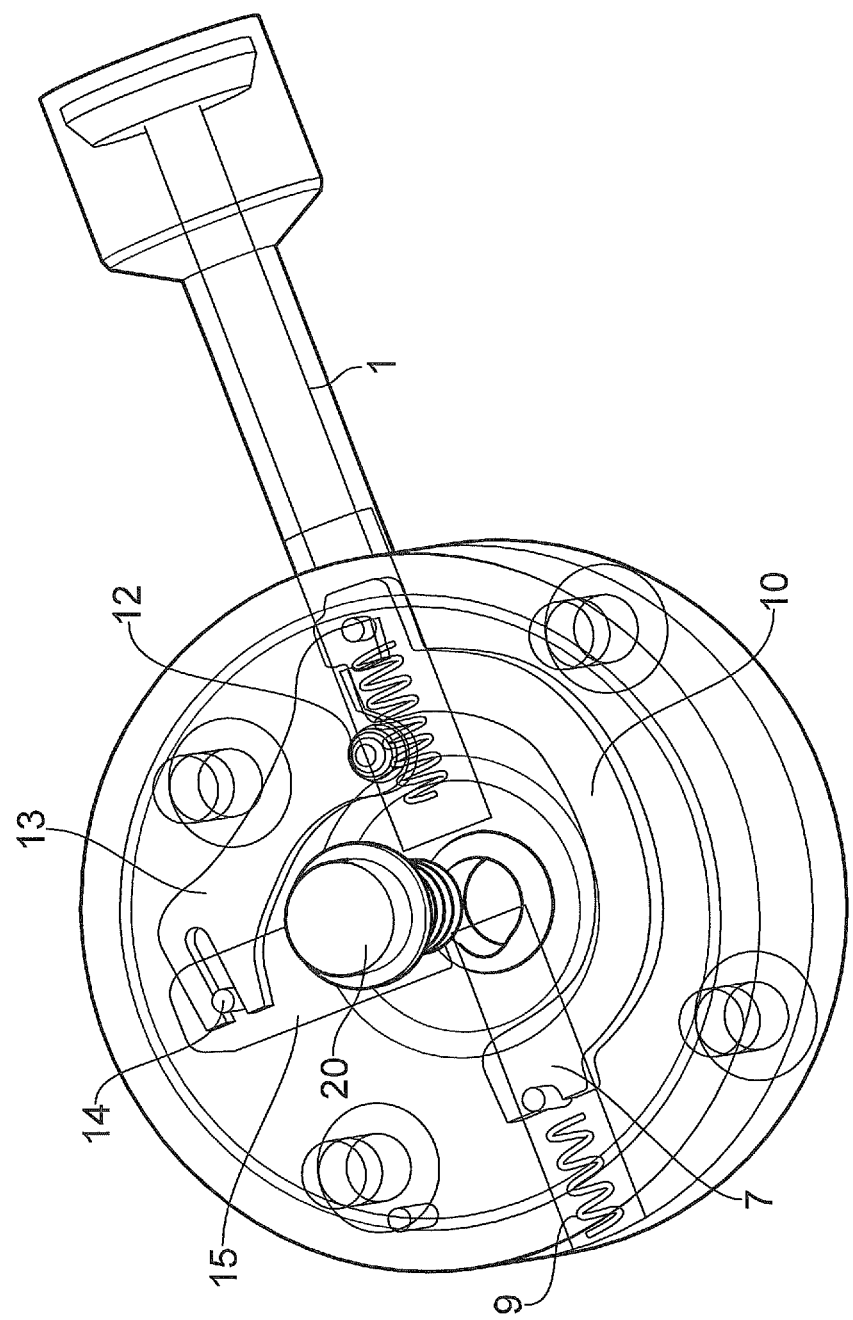
FIG. 6 is a sectional perspective view of the lock according to the invention
Figure 7:
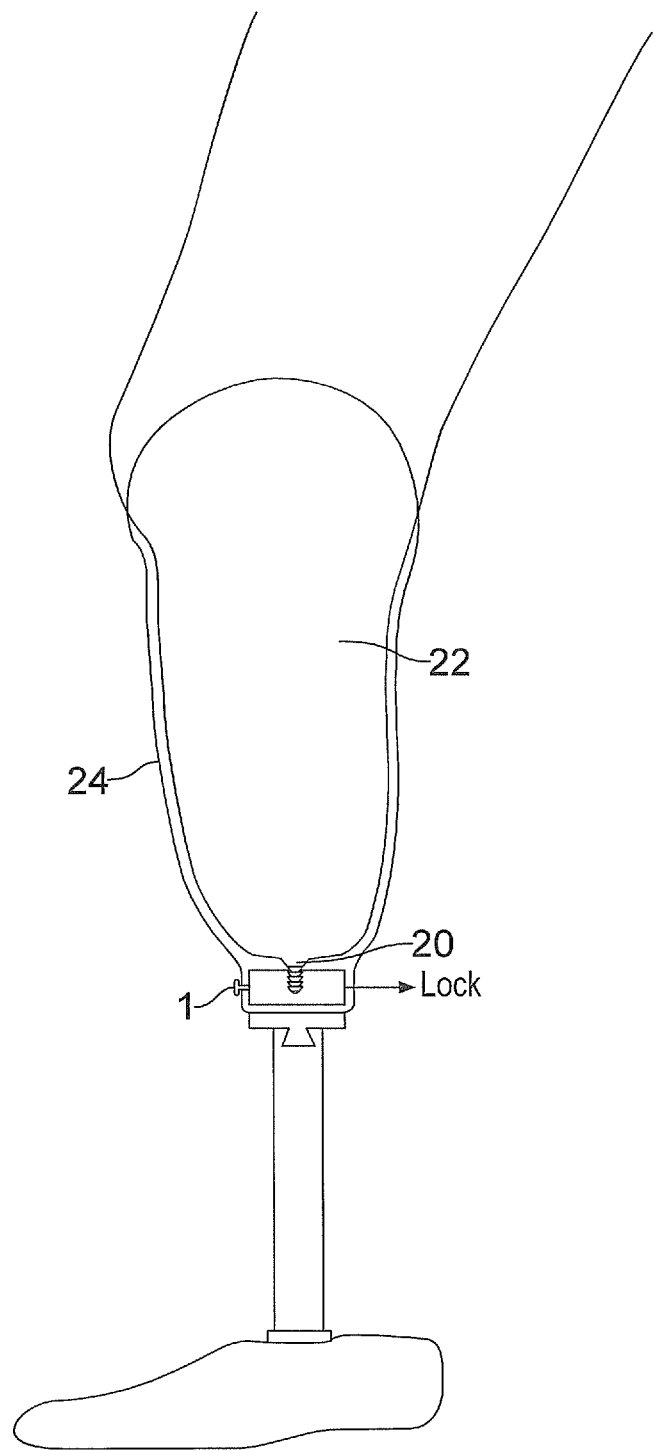
FIG. 7 is an illustration of the locking device in use

A preferred embodiment of the invention is illustrated in use in FIGS. 1 through 6. As can be seen in FIG. 7, an amputee has pulled a silicon stocking (22) over the amputation stump. The silicon stocking is equipped with a locking pin (20) at its lower end. The user inserts the amputation stump into the moulded upper end (24) of the prosthesis. The lock of the current invention is attached at the bottom of the moulded section (24) using means known in the art. The prosthesis user then pushes the amputation stump down into the prosthetic sleeve, until the locking pin (20) engages the locking mechanism of the current invention.

Figure 1:
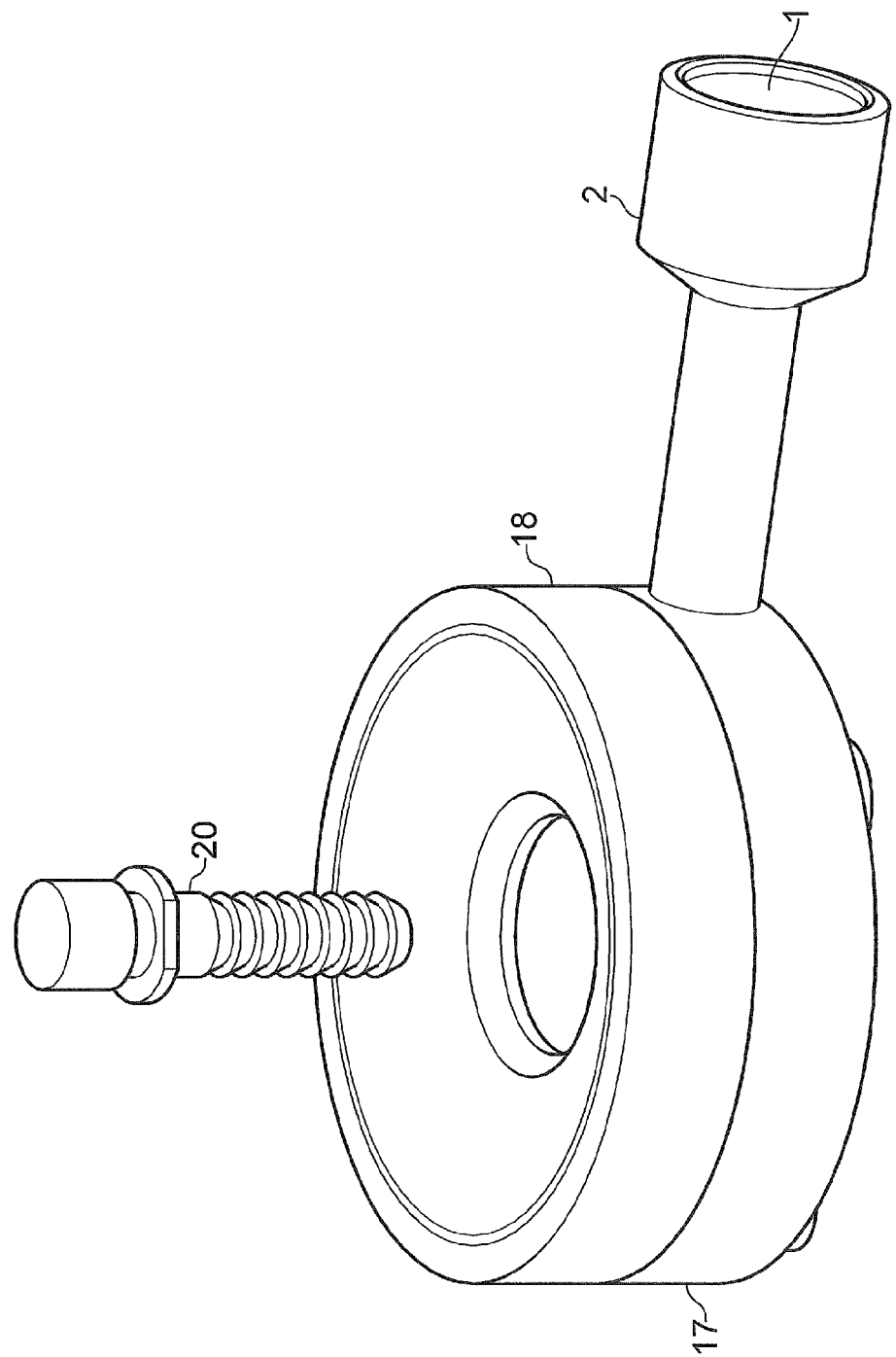
FIG. 1 is a perspective view of the lock according to the invention
Figure 2:
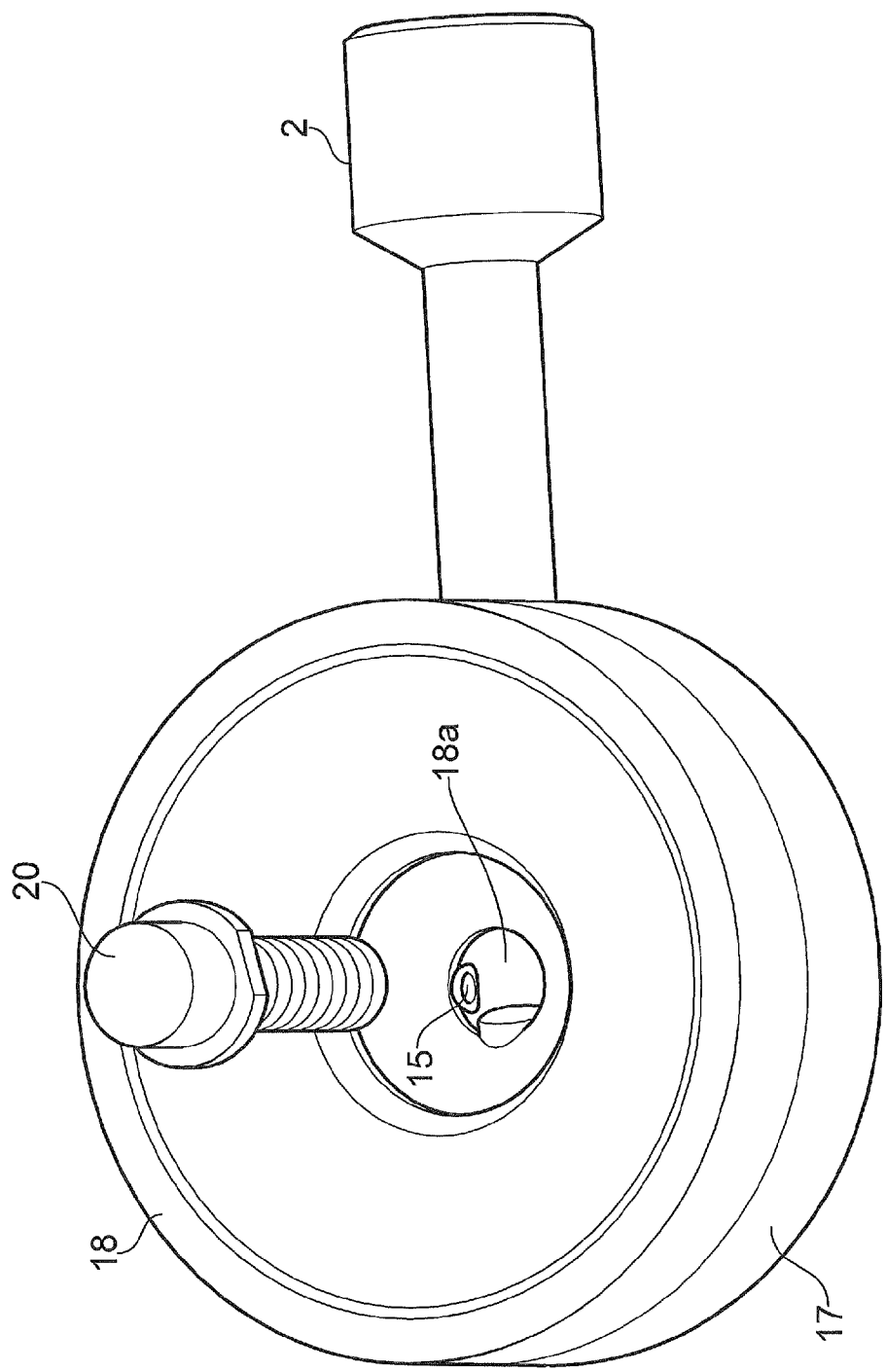
FIG. 2 is a perspective view of the lock according to the invention
Figure 3:
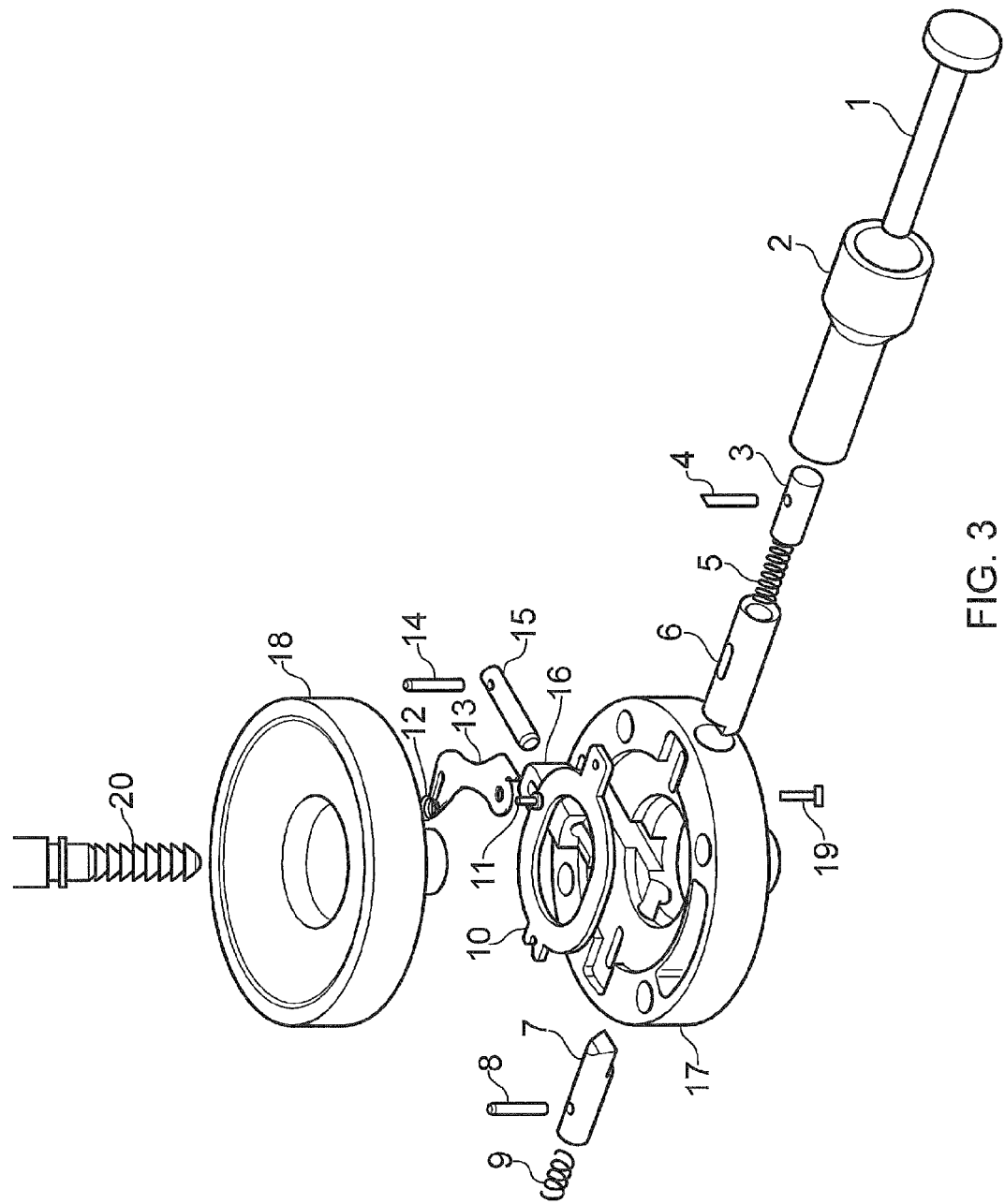
FIG. 3 is an exploded view of the lock according to the invention
Figure 4:
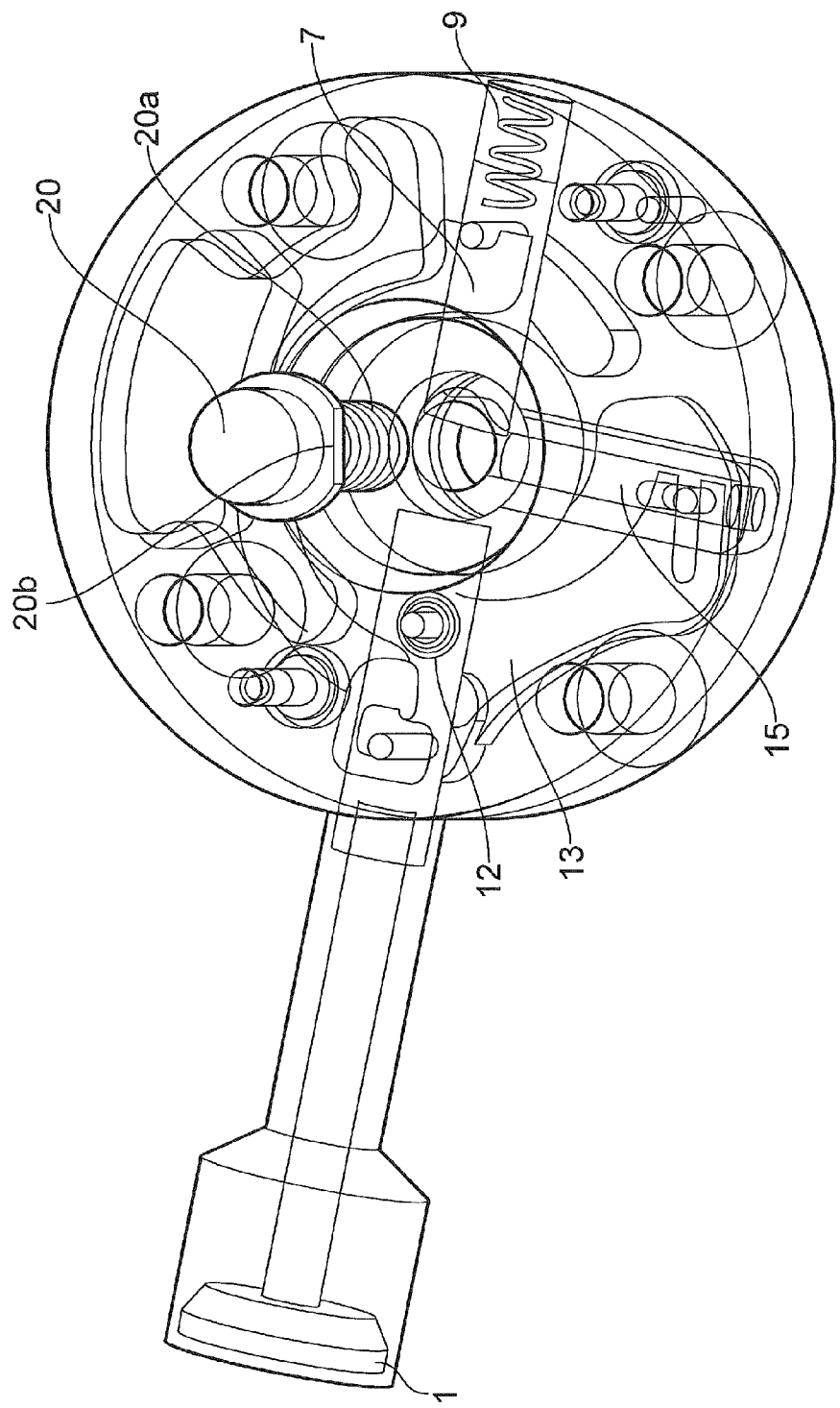
FIG. 4 is a sectional perspective view of the lock according to the invention
Figure 5:
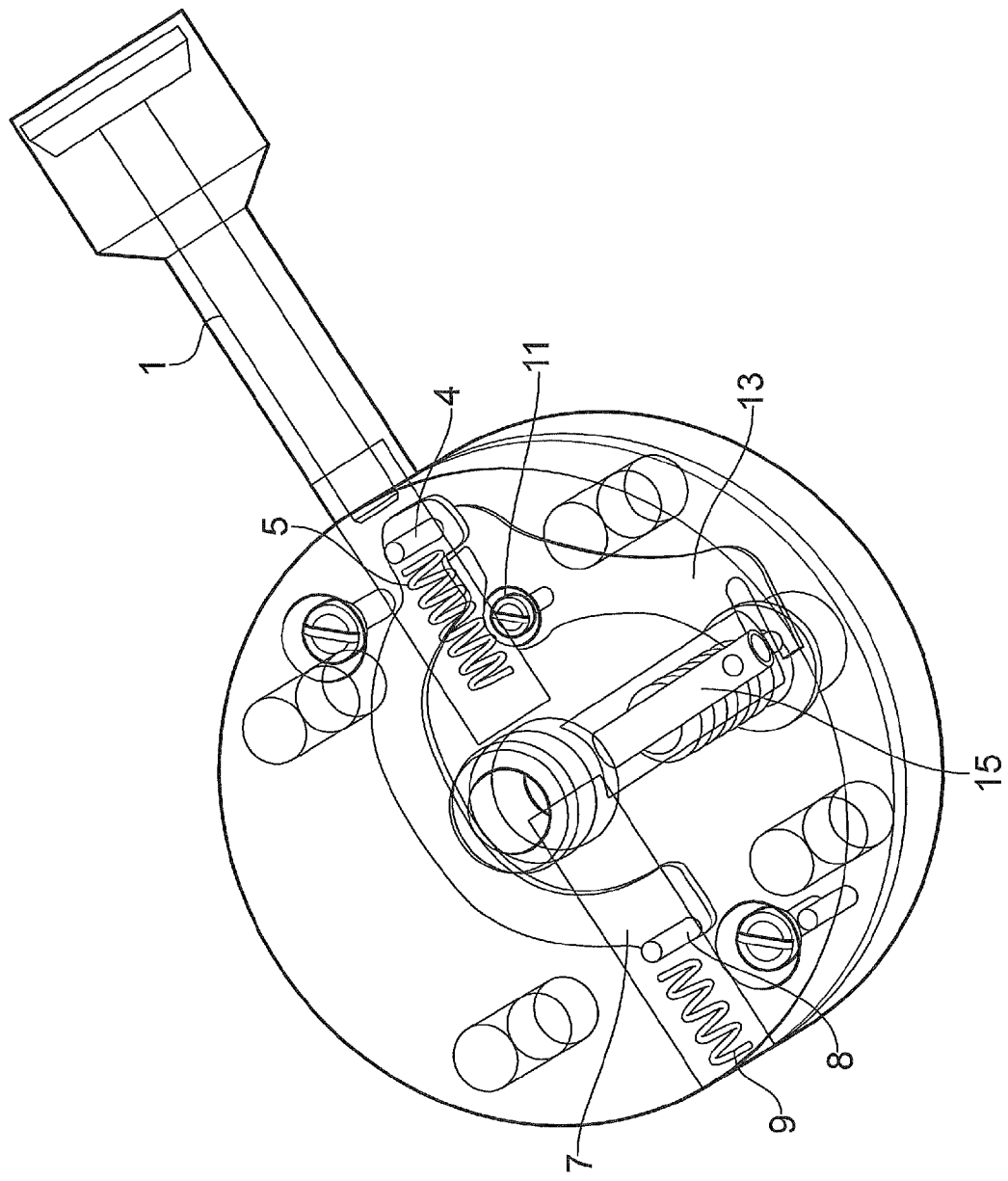
FIG. 5 is a sectional perspective view of the lock according to the invention

The lock according to the invention is illustrated in the drawings, where FIG. 3 is an exploded view of the lock and FIGS. 1 and 2 are views of the assembled lock. The lock comprises of two main parts, a top part (18) and a bottom part (17) which are joined together by means of 2 screws (19). Top part (18) has a central orifice (18a) dimensioned for receiving locking pin (20), and is preferably concave in order to lead the locking pin into the orifice. According to a preferred embodiment the two main components are held together by an additional 4 screws. Material may be advantageously removed at suitable places from parts (18) and (19) in order to reduce the weight. The top part (18) is made of aluminium or another suitable material, the bottom part (17) of black POM or another suitable material.

The lock comprises a release mechanism that is connected with a release button that is arranged passing though the moulded section (24) of the prosthesis to be accessible by the user, and which automatically holds the lock in the open position once engaged by the user. The release mechanism comprises a locking dowel (7) with return spring (9) which engages teeth in the locking pin (20) in the orifice of top part (18) during use, a release button (1) with return spring (5) connected to a stopper release device (3), a release hoop (10), a sensor pin (15) and a locking arm (13). The release loop (10), locking dowel (7), release button (1) and locking arm (13) may be made of steel or another suitable material, while the sensor pin (15) may be made of POM or another suitable material.

The release hoop (10) is located approximately midway between the top part (18) and the bottom part (17) in a countersunk groove and is moveable from side to side in its groove. Release hoop (10) may be in the form of a planar disk or ring having a hole in the center, as shown in FIG. 3, or may be a curved arm as shown in FIG. 6. Release hoop (10) engages locking dowel (7) and the stopper release device (3) via steel pins (4, 8) respectively that stick up from those components. Stopper release device (3) having a steel pin (4) is located in a 2 mm hole and is arranged to engage release hoop (10) on one side of the device, while locking dowel (7) having a steel pin (8) is secured in a 2 mm hole and is moveable in a groove into engagement with the release hoop (10) at the opposite side of the device. Stopper release device (3) may be in an outer position or an inner position. When stopper release device (3) is in the outer position, it will not block the movement of release hoop (10), thus enabling the locking dowel (7) to run free and be pressed by a spring (9) into engagement with locking pin (20).

The device provides means whereby stopper release device (3) is selectively locked into an inner position, which causes release hoop (10) to hold locking dowel (7) in a retracted position, out of engagement with locking pin (20) of the silicon stocking.

Release button (1) may be pressed in by the user. The will move stopper release device (3) towards its inner position. Because pin 4 is connected to release hoop (10), release hoop (10) will move to the side, and move locking dowel (7) out of engagement with locking pin (20). Pin 4 is elongated, and protrudes up past release hoop (10). Pin 4 is arranged to make contact with locking arm (13). Locking arm (13) is arranged in a countersunk groove in the top part (18) and is both tiltable and rotatable. It is secured in the point of rotation by means of an M2 screw (11), while a spring (12) is provided between the locking arm (13) and the top part (18) to facilitate tilting. When pin (4) from stopper release device (3) encounters locking arm (13), it will tilt up locking arm (13) and move past, allowing locking arm (13) to be forced back down by spring (12) once pin (4) has past. When the steel pin (4) located in stopper release device (3) has passed the locking arm (13), the locking arm (13) will return to the starting position by means of the spring (12) and stopper release device (3) will be unable to return to the starting position. The device will thereby be held in an open position, allowing a user to withdraw the amputation stump from the prosthesis.

A sensor pin (15) is provided which senses whether there is a locking pin (20) in the orifice (18a) of top part (18). When a locking pin (20) is in the orifice, sensor pin (15) prevents the locking arm (13) from being able to rotate, thereby keeping stopper release device (3) in an open position via the steel pin (4) which is located in stopper release device (3). When locking pin (20) is pulled out of the lock sensor pin (15) enters into the now vacant orifice. A pin (14) connected to sensor pin (15) causes the locking arm (13) to rotate out of engagement with pin (4), allowing stopper release device (3) to move freely to its outer position. Locking dowel (7) will be pushed back towards the orifice (18a) by means of the spring (9), which in turn moves release hoop (10) and which forces stopper release device (3) back to its outer position. The lock will once again be activated and ready for use.

One skilled in the art will recognize that alternate arrangements of the invention are possible. For example:

1. Instead of a sensor pin which comes out and senses locking pin (20) directly, a pin may be used with an internal magnet. A magnet is therefore employed which is attached to the sensor pin which is shortened so that all parts connected with the sensor pin remain inside the lock. There are therefore no parts of the sensor pin protruding into the centre hole of the lock. The sensing will then be accomplished by the sensor pin being pushed from the centre of the lock by magnetism in the locking pin and the magnet on the sensor pin.

2. The stopper release device (3) may be arranged in communication with locking dowel (7) by other means. For example the release hoop may be cut on one side. This is in order to simplify assembling or dismantling/assembling during repairs.

3. Manual activation of the lock may implemented by having to depress the release button once more. By depressing the release button in order to get the locking pin (20) out, the locking dowel (7) remains in an open position. The second time the release device is pressed, the locking dowel will be released and it will return to an active position.

4. Electronic sensing as to whether the locking pin is in place or not. This may be implemented by using a Hall Effect sensor and magnetic locking pin. When the release device is depressed, a voltage is impressed on the electronics by the activation of the microswitch via the release hoop. A small electromagnet is then employed to pull the locking arm so that the release device is released as the Hall sensor is activated by the magnet in the spike. When the release device returns to the starting position, the microswitch is deactivated by the release hoop returning together with the release device and the electronics being made voltage-free.

The invention claimed is:

1. A locking device for a prosthesis, comprising a main body (17, 18) having an orifice (18a) for receiving a locking pin (20) affixed to a stocking worn by an amputee about the amputation stump, a locking dowel (7) arranged inside the main body, said locking dowel being movable into a locked position in which the locking dowel engages teeth in locking pin (20) and into an unlocked position in which the locking dowel is disengaged from the teeth of the locking pin (20), characterized in that the locking dowel is connected to a release button (1), said release button being arranged, when depressed, to move locking dowel (7) into an unlocked position in which the locking dowel is disengaged from the locking pin, said release button being further engageable with a locking arm (13) when the release button is depressed, the locking arm being arranged to hold the release button, and thereby the locking dowel, in the unlocked position.

2. A locking device according to claim 1, wherein locking dowel (7) is connected to release button (1) via an intermediately arranged, moveable release hoop (10).

3. A locking device according to claim 2, wherein locking dowel (7) is equipped with an upwardly extending pin (8), release button (1) is arranged to move a release stopper device (3) having an upwardly extending pin(4), and wherein pins (4) and (8) abut release hoop (10).

4. A locking device according to claim 3, wherein release hoop (10) is arranged in a countersunk groove in a portion of the main body, and is arranged to move sideways.

5. A locking device according to claim 3 or 4 wherein release hoop (10) is a ring having an opening in its center or a curved arm.

6. A locking device according to claim 1, wherein locking arm (3) is spring loaded and tiltable in response to pressure from pin (4), and wherein pin (4) and locking arm (3) are arranged such that, in response to the inward pressing of release button (1), pin (4) will upwardly tilt locking arm (3), and travel past a portion of locking arm (3), allowing locking arm (3) by means of spring force to tilt back into locking engagement with pin (4).

7. A locking device according to claim 6, wherein the lock further comprises a movable sensor pin (15), one end of which is arranged to move into orifice (18a) when no locking pin (20) is present in said orifice, said sensor pin (15) being further connected to locking arm (13), wherein the movement of sensor pin (15) causes a rotation of locking arm (13), whereby, when a locking pin (20) is present in orifice (18*a*) then sensor pin (15) will hold locking arm (13) in locking engagement with pin (4), and when no locking pin (20) is present in orifice (18*a*) the sensor pin (15) will move into orifice (18*a*) and rotate locking arm (13) out of locking engagement with pin (4).

8. A locking device according to claim 1, wherein release button (1) is elongated, and arranged to protrude from an opening in a side of a moulded, amputation stump receiving portion (24) of a prosthesis.

\* \* \* \* \*